(12) United States Patent
Lorence et al.

(10) Patent No.: US 7,767,200 B2
(45) Date of Patent: Aug. 3, 2010

(54) CANCER TREATMENT USING VIRUSES, FLUOROPYRIMIDINES AND CAMPTOTHECINS

(75) Inventors: Robert M. Lorence, Bethesda, MD (US); Michael S. Roberts, Myersville, MD (US)

(73) Assignee: Wellstat Biologics Corporation, Gaithersburg, MD (US)

(*) Notice: Subject to any disclaimer, the term of this patent is extended or adjusted under 35 U.S.C. 154(b) by 0 days.

(21) Appl. No.: 11/913,362

(22) PCT Filed: Jul. 12, 2006

(86) PCT No.: PCT/US2006/027018

§ 371 (c)(1),
(2), (4) Date: Nov. 1, 2007

(87) PCT Pub. No.: WO2007/011601

PCT Pub. Date: Jan. 25, 2007

(65) Prior Publication Data

US 2008/0193419 A1    Aug. 14, 2008

Related U.S. Application Data

(60) Provisional application No. 60/699,195, filed on Jul. 14, 2005.

(51) Int. Cl.
*A16K 48/00* (2006.01)
*C07K 5/00* (2006.01)

(52) U.S. Cl. ............... 424/93.1; 435/320.1; 514/33; 514/26

(58) Field of Classification Search .......... None
See application file for complete search history.

(56) References Cited

U.S. PATENT DOCUMENTS

| | | | |
|---|---|---|---|
| 4,604,463 | A | 8/1986 | Miyasaka et al. |
| 5,004,758 | A | 4/1991 | Boehm et al. |
| 6,403,569 | B1 | 6/2002 | Achterrath |
| 6,428,968 | B1 | 8/2002 | Molnar-Kimber et al. |
| 7,056,689 | B1 * | 6/2006 | Lorence et al. ............ 435/7.23 |
| 7,223,389 | B2 | 5/2007 | Zakay-Rones et al. |
| 7,279,333 | B2 | 10/2007 | Kaneda |
| 7,427,395 | B2 | 9/2008 | Yamamoto et al. |
| 2002/0071832 | A1 | 6/2002 | Fong et al. |
| 2002/0168344 | A1 | 11/2002 | Coffey et al. |

(Continued)

FOREIGN PATENT DOCUMENTS

WO    94/25627    11/1994

(Continued)

OTHER PUBLICATIONS

ASCO Annual Meeting, abstract No. 1213, 2003.*

(Continued)

*Primary Examiner*—Robert B Mondesi
*Assistant Examiner*—Bao Li
(74) *Attorney, Agent, or Firm*—Douglas A. Golightly (57) ABSTRACT

Mammalian subjects having a neoplasm are treated with a virus, a fluoropyrimidine, for example 5-fluorouracil, and a camptothecin compound. The virus is selected from the group consisting of a Newcastle disease virus, a measles virus, a vesicular stomatitis virus, an influenza virus, a Sindbis virus, a picornavirus, and a myxoma virus.

14 Claims, 4 Drawing Sheets

U.S. PATENT DOCUMENTS

| | | | |
|---|---|---|---|
| 2003/0044384 | A1 | 3/2003 | Roberts et al. |
| 2003/0068307 | A1 | 4/2003 | Yu et al. |
| 2004/0253272 | A1 | 12/2004 | Kaneda |
| 2005/0147591 | A1 | 7/2005 | Hallahan et al. |
| 2006/0165656 | A1 | 7/2006 | Yamamoto et al. |
| 2007/0128170 | A1 | 6/2007 | Zakay-Rones et al. |
| 2007/0207149 | A1 | 9/2007 | Lorence et al. |

FOREIGN PATENT DOCUMENTS

| | | |
|---|---|---|
| WO | 97/12623 A1 | 4/1997 |
| WO | 97/16454 | 5/1997 |
| WO | 97/25332 | 7/1997 |
| WO | 97/28164 | 8/1997 |
| WO | 98/35969 | 8/1998 |
| WO | 99/05103 | 4/1999 |
| WO | 99/17804 | 4/1999 |
| WO | 99/17805 | 4/1999 |
| WO | 99/25860 | 5/1999 |
| WO | WO00/07605 | 2/2000 |
| WO | 00/53607 | 9/2000 |
| WO | 00/62735 | 10/2000 |
| WO | 01/64194 | 9/2001 |
| WO | 01/70275 | 9/2001 |
| WO | 01/76597 | 10/2001 |
| WO | WO03/022202 | 3/2003 |
| WO | 03/086471 | 10/2003 |
| WO | 03/093274 | 11/2003 |
| WO | 03/101406 | 12/2003 |
| WO | 03/101996 | 12/2003 |
| WO | 03/101998 | 12/2003 |
| WO | 2004/000209 | 12/2003 |
| WO | 2004/012661 | 2/2004 |
| WO | 2004/039406 | 5/2004 |
| WO | 2005/051433 A1 | 6/2005 |
| WO | WO2005/113013 | 12/2005 |
| WO | WO2005/115391 | 12/2005 |

OTHER PUBLICATIONS

Smith et al. Exp. Opin. Inves. Drug. 2000, vol. 9, No. 2, pp. 311-327.*

Vanhoefer, et al., "Irinotecan in the Treatment of Colorectal Cancer: Clinical Overview", J. Clin. Oncology, vol. 19, No. 5, pp. 1501-1518, Mar. 2001.

Pecora, et al., "Phase I Trial of Intravenous Administration of PV701, an Oncolytic Virus, in Patients With Advanced Solid Cancers" J. Clin. Oncol. (2002) 20(9): 2251-2266.

Hoff, et al., "The Evolution of Fluoropyrimidine Therapy: From Intravenous to Oral" The Oncologist, (2001) 6(suppl 4):3-11.

Garcia-Carbonero, et al., "Minireview: Current Perspectives on the Clinical Expeience, Pharmacology, and Continued Development of the Camptothecins" Clin. Cancer Research (Mar. 2002) 8: 641-661.

Nemunaitis, et al., "Pilot trial of intravenous infusion of a replication-selective adenovirus (ONYX-015) in combination with chemotherapy or IL-2 treatment in refractory cancer patients" Cancer Gene Therapy (2003) 10: 341-352.

Kelly, et al., "Camptothecin: an Inhibitor of Influenza Virus Replication", J. Gen. Virol (1974) 25: 427-432.

Meck, et al., "A Virus-directed Enzyme Prodrug Therapy Approach to Purging Neuroblastoma Cells from Hematopoietic Cells Using Adenovirus Encoding Rabbit Carboxylesterase and CPT-11", Cancer Research, (2001) 61: 5083-5089.

Pizzolato, et al., "The Camptothecins", The Lancet, (2003) 361: 2235-2242.

Ulukan, et al., "Camptothecins: A Review of Their Chemotherapeutic Potential", Drugs, (Jul. 2002) 62(14): 2039-2057.

Teufel, et al., "Irinotecan plus folinic acid/continuous 5-fluorouracil as simplified bimonthly FOLFIRI regimen for first-line therapy of metastatic colorectal cancer", BMC Cancer, (Jul. 2004) 4(38): 1-8.

Tournigand, et al., "FOLFIRI followed by FOLFOX6 or the reverse sequence in advanced colorectal cancer: A randomized GERCOR study", (Jan. 2004) 22(2): 229-237.

Andre, et al., "CPT-11 (Irinotecan) Addition to Bimonthly, High-dose Leucovorin and Bolus and Continuous-infusion 5-Fluorouracil (FOLFIRI) for Pretreated Metastatic Colorectal Caner", (1999), 35(9): 1343-1347.

Colucci, et al., "Phase III Randomized Trial of FOLFIRI Versus FOLFOX4 in the Treatment of Advanced Colorectal Cancer: A Multicenter Study of the Gruppo Oncologico Dell'Italia Meridionale", (Aug. 2005), 23(22): 4866-4875.

Bouche, et al., "Randomized Multicenter Phase II Trial of a Biweekly Regimen of Fluorouracil and Leucovorin (LV5FU2), LV5FU2 Plus Cisplatin, or LV5FU2 Plus Irinotecan in Patients with Previously Untreated Metastatic Gastric Caner: A Federation Francophone de Cancerologie Digestive Group Study—FFCD 9803", Journal of Clinical Oncology, (Nov. 2004), 22(21): 4319-4328.

Ducreux, et al., "Irinotecan Combined with Bolus Fluorouracil, Continuous Infusion Fluorouracil, and High-Dose Leucovorin Every Two Weeks (LV5FU2 Regimen): A Clinical Dose- Finding and Pharmacokinetic Study in Patients with Pretreated Metastatic Colorectal Cancer", Journal of Clinical Oncology, (1999), 17(9): 2901-2908.

Kohne, et al., "Phase III Study of Weekly High-Dose Infusional Fluorouracil Plus Folinic Acid with or without Irinotecan in Patients with Metastatic Colorectal Cancer: European Organisation for Research and Treatment of Gastrointestinal Group Study 40986", Journal of Clinical Oncology, (Aug. 2005), 23(22) 4856-4865.

Goto, et al, "Phase I/II study of irinotecan, 5-fluorouracil, and I-Leucovorin combination therapy (modified Saltz regiment) in patients with metastatic colorectal cancer", Int. J. Clinical Oncology, (Oct. 2004) 9: 364-368.

Sastre, et al., "A phase I, dose-finding study of irinotecan (CPT-11) short i.v. infusion combined with fixed dose of 5-fluorouracil (5-FU) protracted i.v. infusion in adult patients with advanced solid tumours", Cancer Chemother Pharmacol, (May 2005) 55: 453-460.

Petty, et al., "Novel Fluoropyrimidines: Improving the Efficacy and Tolerability of Cytotoxic Therapy", Current Cancer Drug Targets, (Mar. 2004), 4: 191-204.

Lamont, et al., "The Oral Fluoropyrimidines for Cancer Chemotherapy", Clinical Cancer Research, (1999), 5: 2289-2296.

Rustum, et al., "Rationale for Treatment Design: Biochemical Modulation of 5-Fluorouracil by Leucovorin", The Cancer Journal from Scientific America, (1998), 4(1): 12-18.

Vincent, et al., "Which 5-Fluorouracil regime?—the great debate", Anti-Cancer Drugs, (1999), 10: 337-354.

Saltz, et al., "Phase I Clinical and Pharmacokinetic Study of Irinotecan, Fluorouracil, and Leucovorin in Patients with Advanced Solid Tumors", Journal of Clinical Oncology, (1996), 14(11): 2959-2967.

Jolivet, et al., "Role of Leucovorin Dosing and Administration Schedule", European Journal of Cancer, (1995), 31A (7/8): 1311-1315.

Lorence, et al., "Overview of phase I studies of intravenous administration of PV701 an oncolytic virus", Current Opinion in Molecular Therapeutics 2003, vol. 5(6), 618-624.

Laurie, et al., "A Phase 1 Clinical Study of Intravenous Administration of PV701, an Oncolytic Virus, Using Two-Step Desensitization", Clinical Cancer Research, (Apr. 2006) 12(8), 2555-2562.

International Search Report dated Aug. 14, 2007.

International Preliminary Report on Patentability dated Jan. 24, 2008.

U.S. Appl. No. 60/565,631, filed Apr. 27, 2004.

Atherton and Burke, "Interferon Induction by viruses and polynucleotides: a differential effect of camptothecin", (1975) J. Gen. Virol. 29:297-304.

Negoro et al. "A phase II study of CPT-11, a camptothecin derivative, in patients with primary lung cancer. CPT-11 Cooperative Group Study" Gan to Kagaku Ryoho (Japanese Journal of Cancer & Chemotherapy) (1991) 18:1013-1019. (Abstract only).

Shah et al. "Oncolytic viruses: clinical applications as vectors for the treatment of malignant gliomas" J Neurooncol. Dec. 2003; 65:203-26.

Ring, "Cytolytic viruses as potential anti-cancer agents" J Gen Virol. (2002) 83:491-502.

Heideman, "Gene Therapy and Virotherapy of Gastric Cancer: Preclinical Results and Clinical Development", Digestive Diseases, 22(4):374-379, 2004.

Hasenburg, et al., "Thymidine kinase gene therapy with concomitant topotecan chemotherapy for recurrent ovarian cancer" Cancer Gene Therapy,7(6): 839-852, 2000.

Robert M. Lorence, "Continuing the Interaction Between Non-Clinical and Clinical Studies" slides presented at Oncolytic Viruses meeting in Banff, Alberta, Canada; slide #25 on p. 5, Mar. 12, 2005.

Horwitz, et al., "Antiviral Action of Camptothecin", Antimicrobial Agents and Chemotherapy, 2(5): 395-401, 1972.

Mendelsohn, et al., "Status of Epidermal Growth Factor Receptor Anatgonists in the Biology and Treatment of Cancer", Journal of Clinical Oncology, 21(14): 2787-2799, 2003.

Alexander, "Chapter 27: Newcastle Disease" A Laboratory Manual for the Isolation and Identification of Avian Pathogens, 3rd Edition, Kendal/Hunt, 114-120, 1989.

Kirn, "Virotherapy for Cancer: Current Status, Hurdles, and Future Directions", Cancer Gene Therapy, 9: 959-960, 2002.

Bell, "Oncolytic Viruses: Programmable Tumour Hunters", Current Gene Therapy, 2(2): 243-254, 2002.

Cats, "New Developments in Systemic Chemotherapy in Advanced Colorectal Cancer", Scand J Gastroenterol, Suppl 239: 78-86, 2003.

Prewett, et al., "Enhanced Antitumor Activity of Anti-epidermal Growth Factor Receptor Monoclonal Antibody IMC-C225 in Combination with Irinotecan (CPT-11) against Human Colorectal Tumor Xenografts", Clinical Cancer Research, 8: 994-1003, May 2002.

Phuangsab, et al., "Newcastle disease virus therapy of human tumor xenografts: antitumor effects of local or systemic administration", Cancer letters, 172: 27-36, 2001.

U.S. Appl. No. 11/568,228, Office Action dated Dec. 24, 2008.

Heise et al. "ONYX-015, an E1B gene-attenuated adenovirus, causes tumor-specific cytolysis and antitumoral efficacy that can be augmented by standard chemotherapeutic agents" Nature Medicine (1997) 3(6):639-645.

Chahlavi et al. "Replication-competent Herpes Simplex virus vector G207 and cisplatin combination therapy for head and neck squamous cell carcinoma" (1999) Neoplasia 1(2):162-169.

Wildner et al. "Therapy of colon cancer with oncolytic adenovirus is enhanced by the addition of herpes simplex virus-thymidine kinase" (1999) Cancer Research 59:410-413.

U.S. Appl. No. 11/568,228, Office Action dated Aug. 5, 2009.

* cited by examiner

CANCER TREATMENT USING VIRUSES, FLUOROPYRIMIDINES AND CAMPTOTHECINS

BACKGROUND OF THE INVENTION

Coadministration of certain viruses with 5-fluorouracil to treat cancer is disclosed in WO 94/25627 (page 12.)

Coadministration of oncolytic viruses with camptothecins is disclosed in WO 2005/113018 (Wellstat Biologics Corp.). The treatment of cancers using certain mutant herpes viruses in combination with any of numerous anticancer agents, including irinotecan and topotecan, is disclosed in U.S. Patent Publication No. 2002/0071832 (Fong, et al.), paragraphs 7 and 40. Methods of treating neoplasias using target cell-specific adenoviral vectors in combination with antineoplastic agents, including irinotecan or topotecan, are disclosed in U.S. Patent Publication No. 2003/0068307 (Yu, et al.) page 13. See also Nemunaitis, et al., Cancer Gene Ther. (2003) 10(5): 341-352; and Meck, et al., Cancer Res. (2001) 61(13): 5083-5089.

Coadministration of irinotecan, 5-fluorouracil (5-FU) and leucovorin (LV) is disclosed in: Teufel et al., 2004 (BMC Cancer 4:38); Tournigand et al., 2004 (J Clin Oncol 2:229-237); Andre et al., 1999 (Eur J Cancer 35:1343-7); Colucci et al., 2005 (J Clin Oncol 22); Bouche et al., 2004 (J Clin Oncol 22:4319-4328); Ducreux et al, 1999 (J Clin Oncol 17:2901-8); Kohne et al., 2005 (J Clin Oncol 23); Saltz et al., 1996 (J Clin Oncol 14:2959-67); Goto et al., 2004 (Int J Clin Oncol 9:354-8). Additional combinations of irinotecan and 5-FU are listed in Table 3 of Vanhoefer et al., 2001 (J Clin Oncol 19:1501-18) and in Sastre et al., 2005 (Cancer Chemother Pharmacol 55:453-60).

SUMMARY OF THE INVENTION

This invention provides a method for treating a mammalian subject having a neoplasm, comprising administering to the subject a virus, a fluoropyrimidine compound and a camptothecin compound in a combined amount effective to treat the subject; wherein the virus is selected from the group consisting of a Newcastle disease virus, a measles virus, a vesicular stomatitis virus, an influenza virus, a Sindbis virus, a picornavirus, and a myxoma virus.

This invention provides for the use of a virus and/or a fluoropyrimidine and/or a camptothecin compound in the manufacture of a medicament for treating, in combination with the other ingredients mentioned, a subject having a neoplasm; wherein the virus is selected from the group consisting of a Newcastle disease virus, a measles virus, a vesicular stomatitis virus, an influenza virus, a Sindbis virus, a picornavirus, and a myxoma virus. The medicament can contain one, two or all three of the ingredients listed.

DETAILED DESCRIPTION OF THE INVENTION

As used herein the transitional term "comprising" is open-ended. A claim utilizing this term can contain elements in addition to those recited in such claim. Thus, for example, the claims can read on treatment regimens that also include other therapeutic agents or therapeutic virus doses not specifically recited therein, as long as the recited elements or their equivalent are present.

As used herein "NDV" is an abbreviation for Newcastle Disease Virus. As used herein "DLT" is an abbreviation for dose limiting toxicity. As used herein the term "plaque-forming unit" (PFU) means one infectious virus particle. As used herein "BPFU" means billion PFUs. As used herein "PP" means plaque-purified. Thus, for example PPMK107 means plaque-purified Newcastle Disease virus strain MK107. As used herein "PFU/m$^2$", which is a standard unit for expressing dosages, means PFUs per square meter of patient surface area. As used herein the term "replication-competent" virus refers to a virus that produces infectious progeny in cancer cells.

In an embodiment of this invention the virus is replication-competent.

In accordance with this invention, when the virus is a Newcastle Disease Virus it can be of low (lentogenic), moderate (mesogenic) or high (velogenic) virulence. The level of virulence is determined in accordance with the Mean Death Time in Eggs (MDT) test. (Alexander, "Chapter 27: Newcastle Disease" in Laboratory Manual for the Isolation and Identification of Avian Pathogens, 3$^{rd}$ ed., Purchase, et al. eds. (Kendall/Hunt, Iowa), page 117.) Viruses are classified by the MDT test as lentogenic (MDT>90 hours); mesogenic (MDT from 60-90 hours); and velogenic (MDT<60 hours). Mesogenic NDV is currently preferred.

In accordance with this invention, any conventional route or technique for administering viruses to a subject can be utilized. For examples of routes of administration refer to WO 00/62735. In one embodiment of this invention, the virus is administered systemically, for example intravenously. For intravenous administration of a therapeutic virus in accordance with this invention, preferably the virus is a mesogenic strain of Newcastle Disease Virus. In a preferred embodiment of this invention, from $12 \times 10^9$ to $120 \times 10^9$ PFU/m$^2$ per dose of a mesogenic strain of Newcastle Disease virus is administered intravenously to a human subject, more preferably from $12 \times 10^9$ to $48 \times 10^9$ PFU/m$^2$ per dose. As used herein "mg/m$^2$" means milligrams per square meter of patient surface area.

In embodiments of this invention the picornavirus is a poliovirus, an echovirus, or a coxsackievirus. Examples of coxsackieviruses that are suitable in accordance with this invention include the following types: A21, A13, A15 and A18. Examples of suitable echoviruses include echovirus type 1.

The use of fluoropyrimidines as anticancer agents is reviewed in Petty & Cassidy (2004) Curr. Cancer Drug Targets, 4:191-204; and Lamont and Schilsky (1999) Clin. Cancer Res. 5:2289-2296. These agents are fluorinated pyrimidines which have antitumor activity through several mechanisms including inhibition or RNA synthesis and function, inhibition of thymidylate synthase activity and incorporation into DNA.

As used herein the terms "fluoropyrimidine" or "fluoropyrimidine compound" mean one or more of the following: 5-fluorouracil (5-FU); capecitabine; 5-fluoro-2'-deoxyuridine (FudR); ftorafur; emitefur; eniluracil/5-FU; S-1 (a combination of the 5-FU prodrug ftorafur and two 5-FU modulators called 5-chloro-2,4-dihydroxypuridine and oxonic acid in a molar ratio of 1:0.4:1); and UFT (a combination of ftorafur, and uracil in a 1:4 molar ratio) (Lamont and Schilsky, 1999). 5-FU is often given with the drug leucovorin to enhance the cytotoxic effects of 5-FU (see, for example, Jolivet, 1995, Eur J Cancer 31A:1311-1315 and Rustum et al., 1998; Cancer J Sci Am 4:12-18). The dosing and administration techniques and schedules for fluoropyrimidines and for Leucovorin are well known in the art (See, e.g. Vincent et al., 1999 (Anticancer Drugs 10:337-54); Jolivet, 1995), and their optimization for a specific patient is within the ability of the skilled clinician. Bolus dosing with 5-FU is usually administered to human patients in a dosage amount of from 370 to 500 mg/m² daily for 5 days every 4 to 5 weeks, or more preferably 500 mg/m² weekly. In an embodiment of this invention one or more doses of 5-fluorouracil are given by continuous infusion over a period of at least 22 hours per dose. Continuous dosing with 5-FU includes an intravenous bolus dose of 400 mg/m² followed by 600 mg/m² over 22 hours. In another embodiment, a bolus dose of 400 mg/m² is followed by a dose of 2400 mg/m² administered over 46 hours. Leucovorin is usually administered to human patients in a dosage amount of from 200 to 500 mg/m² administered immediately prior to or during the 5-FU doses.

The use of camptothecins as anticancer agents is reviewed in Garcia-Carbonero, et al., Clin. Cancer Res. (March 2002) 8: 641-661; and in Pizzolato J F and Saltz L B, The camptothecins. Lancet 2003 361:2235-42. Camptothecins have antitumor activity based on their binding to and inhibition of topoisomerase I, a nuclear enzyme which reduces torsional stress during DNA replication and which has an important role in DNA replication. Topotecan and irinotecan have been approved for clinical use by the U.S. Food and Drug Administration (FDA). Other camptothecins are in development as cancer therapeutics (Ulukan and Swaan, (Campothecins: a review of their chemotherapeutic potential. Drugs, 2002, 62:2039-57); and Garcia-Carbonero and Supko, 2002).

As used herein the term "camptothecin compound" means that class of compounds considered to be camptothecins, camptothecin analogs, camptothecin derivatives or camptothecin conjugates. These compounds are based on the characteristic five-ring backbone of camptothecin:

In accordance with this invention any camptothecin compound can be utilized. Examples of camptothecin compounds include irinotecan (CAMPTOSAR; 7-ethyl-10-[4-(1-piperidino)-1-piperidino]-carbonyloxycamptothecin), topotecan (HYCAMPTIN; (S)-9-N,N-dimethylaminoethyl-10-hydroxycamptothecin), 9-aminocamptothecin (9-amino-20(S)-camptothecin), 9-nitrocamptothecin (also called rubitecan), lurtotecan (7-(4-methylpiperazinomethylene)-10,11-ethylenedioxy-20(S)-camptothecin), exatecan, karenitecin, and a homocamptothecin. The structures and clinical information for some camptothecin compounds can be found in Garcia-Carbonero, et al., Clin. Cancer Res. (March 2002) 8: 641-661. Examples of camptothecin compounds can also be found in U.S. Pat. No. 4,604,463,U.S. Pat. No. 6,403,569, and U.S. Pat. No. 5,004,758, and in WO 2004/012661, WO 2003/101998, WO 2003/101996, WO 2003/101406, WO 2003/093274, WO 2003/086471, WO 01/76597, WO 01/64194, WO 00/70275, WO 00/53607, WO 99/17805, WO 99/17804, WO 99/05103, WO 98/35969, WO 97/28164, WO 97/25332, WO 97/16454, the contents of all of which are incorporated herein by reference.

In accordance with the combination therapy of this invention the camptothecin compound can be administered from one month before administration of the virus until one month after administration of the virus. In more specific embodiments the camptothecin compound and the virus are administered to the subject within a single twenty-four hour period; or the camptothecin compound is administered from twenty-four hours to one month, preferably from twenty-four hours to one week, before administration of the virus; or the camptothecin compound is administered to the subject from twenty-four hours to one month, preferably from twenty-four hours to one week, after administration of the virus.

"Chemotherapy is generally given at regular intervals called cycles. A cycle may involve one dose followed by several days or weeks without treatment. This allows normal cells in the body time to recover from the drug's side effects. Alternatively, doses may be given several days in a row, or every other day for several days, followed by a period of rest . . . the number of cycles . . . may be determined before treatment starts . . . or may be flexible, in order to take into account how the treatment affects the cancer." (from "Planning Drug Doses and Schedules", on website of American Cancer Society, visited May 23, 2005). In an embodiment of this invention the virus, fluoropyrimidine and camptothecin compounds are administered in one or more cycles, more preferably two or more cycles. A single cycle can last, for example, for 8 weeks, 6 weeks, 30 days, or 3 weeks.

Tables 3 through 6 below show representative dosing schedules, which are also suitable in connection with viruses, fluoropyrimidines and camptothecins other than the exemplified ones, for administering amounts that are the same or different as shown in the examples. Accordingly, in further embodiments of this invention, the virus, fluoropyrimidine, and camptothecin compounds are administered in a cycle according to the schedule shown in any one of Tables 3 through 6.

The dosing and administration techniques and schedules for camptothecins and anti-cancer viruses are known in the art (See, e.g. Garcia-Carbonero, et al.; WO 00/62735; WO 2004/000209; and Pecora, et al., J. Clin. Oncol. (2002) 20(9): 2251-2266), and their optimization for a specific patient is within the ability of the skilled clinician. Irinotecan is usually administered to human patients in a dosage amount of from 62.5 to 125 mg/m² four times per week, or more preferably 80 to 125 mg/m² four times per week; or from 300 to 350 mg/m² once every three weeks, or more preferably 300 to 350 mg/m² once every three weeks.

The subject that is treated in accordance with this invention can be either a human subject or a non-human mammalian subject. In accordance with this invention, any neoplasm can be treated, including but not limited to the following: rectal cancer, pelvic cancer, colon cancer, lung cancer, breast cancer, prostate cancer, glioblastoma, renal cancer, pancreatic cancer, head and neck cancer, endometrial cancer, neuroblastoma, carcinoid, melanoma, ovarian cancer, sarcoma, cancer of the gastro-esophageal junction, gastric cancer, esophageal cancer, liver cancer, and cervical cancer.

Although monitoring the treatment is not an essential aspect of the invention, there are techniques for measuring the therapeutic effects of the treatment. These include, measuring the size of the tumor after administration of the virus, and a decrease in tumor size is a positive result.

The invention will be better understood by reference to the following examples, which illustrate but do not limit the invention described herein. In the following examples the NDV is a triple-plaque purified MK107, which is an attenuated (mesogenic) version of Newcastle Disease Virus, described more fully in International Patent Publication WO 00/62735, published Oct. 26, 2000 (Pro-Virus, Inc.). The entire contents of WO 00/62735 and U.S. Provisional Application No. 60/565,631, filed Apr. 27, 2004 are hereby incorporated herein by reference.

EXAMPLES

Example 1

NDV in Combination with 5-Fluorouracil. (5-FU)

Athymic mice were injected subcutaneously with 10 million human HT1080 fibrosarcoma cells. Seven days later when the tumors were approximately 120 to 150 mm$^3$ in size, animals were randomized and treated with one of 10 different treatment regimens (see Table 1 for details) that included suboptimal doses of intravenous NDV (2E+07 or 1E+08 PFU), 100 mg/kg of bolus 5-fluorouracil (5-FU) given intraperitoneally, and subcutaneous implantation of a pellet containing 5 mg of 5-FU (Catalog #Z-190, Innovative Research of America; Sarasota, Fla.) or placebo pellets (Catalog #C-111, Innovative Research of America; Sarasota, Fla.) and other vehicle controls. If pellets were implanted these were performed at a remote site from the subcutaneous tumors. The date of the first treatment is indicated as Day 0 in Table 1 below. 5-FU pellets were used to provide a slower release of 5-FU than bolus dosing. These 5-FU pellets were used to approximate the effects of continuous infusion of 5-FU or administration of an oral analog of 5-FU such as capecitabine over several days.

TABLE 1

Treatment regimens tested in tumor-bearing athymic mice.

| Group | Number of Mice | Treatment, Day 0 | Treatment, Day 2 | Treatment, Day 4 |
|---|---|---|---|---|
| 1 | 11 | M/L$^a$ | 5FU pellet | M/L$^a$ |
| 2 | 11 | M/L$^a$ | Pellet control | M/L$^a$ |
| 3 | 11 | M/L$^a$ | 5FU pellet | NDV, 1E+08 |
| 4 | 11 | M/L$^a$ | Pellet control | NDV, 1E+08 |
| 5 | 11 | M/L$^a$ | 5FU bolus | NDV, 1E+08 |
| 6 | 11 | M/L$^a$ | 5FU bolus | M/L$^a$ |
| 7 | 11 | M/L$^a$ | Bolus control$^b$ | NDV 1E+08 |
| 8 | 11 | M/L$^a$ | Bolus control$^b$ | M/L$^a$ |
| 9 | 11 | NDV, 2E+07 | 5FU bolus | M/L$^a$ |
| 10 | 11 | NDV, 2E+07 | Bolus control$^b$ | M/L$^a$ |

$^a$M/L: Mannitol (5%)/lysine (1%) vehicle control
$^b$Bolus control: Water for injection The incidence of complete tumor regression (CR, 100% tumor reduction was much higher in the group receiving both NDV and 5-FU (whether by bolus dosing or by pellet) than either 5-FU alone or NDV alone see Tables 2a-c.

TABLE 2a

Treatment of tumor-bearing mice with bolus 5-FU two days after treatment with NDV yields greater tumor responses than either agent alone.

| Group | Treatment | Complete Tumor Responses (CR), % |
|---|---|---|
| 6 | Bolus 5-FU | 0% |
| 8 | Control bolus | 0% |
| 9 | Both NDV and bolus 5-FU | 63% |
| 10 | NDV and control bolus | 18% |

TABLE 2b

Treatment of tumor-bearing mice with bolus 5-FU two days before treatment with NDV yields greater tumor responses than either agent alone.

| Group | Treatment | Complete Tumor Responses (CR), % |
|---|---|---|
| 5 | Both NDV and bolus 5-FU | 36% |
| 6 | Bolus 5-FU | 0% |
| 7 | NDV and control bolus | 0% |
| 8 | Control bolus | 0% |

TABLE 2c

Treatment of tumor-bearing mice with a 5-FU pellet two days before treatment with NDV yields greater tumor responses than either agent alone.

| Group | Treatment | Complete Tumor Responses (CR), % |
|---|---|---|
| 1 | Pellet 5-FU | 0% |
| 2 | Control Pellet | 0% |
| 3 | Both NDV and pellet 5-FU | 27% |
| 4 | NDV and control pellet | 0% |

Example 2

NDV in Combination with Irinotecan, 5-Fluorouracil (5-FU) and Leucovorin

Cancer patients are treated with NDV followed by treatment with irinotecan, leucovorin and 5-fluorouracil. In each 6 week cycle, NDV treatment consist of 9 to 12 total intravenous treatments given over 5 weeks followed by a one week rest period (see Table 3 below). The first dose of each cycle consists of 12 to 24 billion PFU/m$^2$ (administered over 3 hours for course 1 and over 1 hour for all other courses) followed by additional doses of between 24 to 48 billion PFU/m$^2$ (each dose administered over 1 hour). Irinotecan (180 mg/m$^2$ over 90 minutes intravenously) is given every other week beginning during week 2 of cycle 1 (As an example, see Table 8 below). Leucovorin (400 mg/m$^2$ over 120 minutes intravenously) is given concurrently with each dose of irinotecan and followed immediately afterwards by an intravenous bolus dose of 5-FU (400 mg/m$^2$) and then a continuous intravenous infusion of 5-FU (2400 mg/m$^2$) over 46 hours using an intravenous pump. Additional 6 week courses (also termed cycles) of NDV, irinotecan, 5-FU and leucovorin are given to the patients.

TABLE 3

Combination of treatment of NDV using irinotecan (80 to 125 mg/m$^2$), leucovorin, and 5-FU. Cycles of treatment are repeated every 6 weeks.

| Cycle | Week | NDV? | Irinotecan/Leucovorin/5FU? |
|---|---|---|---|
| 1 | 1 | Yes, two doses | No |
|   | 2 | Yes, two to 3 doses | No |
|   | 3 | Yes, two to 3 doses | Yes |
|   | 4 | Yes, one to 2 doses | No |
|   | 5 | Yes, two to 3 doses | Yes |
|   | 6 | No | No |
| 2 | 1 | Yes, two doses | Yes |
|   | 2 | Yes, two to 3 doses | No |
|   | 3 | Yes, two to 3 doses | Yes |
|   | 4 | Yes, one to 2 doses | No |
|   | 5 | Yes, two to 3 doses | Yes |
|   | 6 | No | No |

Example 3

NDV in Combination with Irinotecan, 5-Fluorouracil (5-FU) and Leucovorin

Colorectal cancer patients are treated as in Example 2 with the NDV, irinotecan, leucovorin and 5-fluorouracil with the schedule as given as in Tables 4-6 below. In each 6 week cycle, NDV treatment consist of 10 total intravenous treatments given over 5 weeks followed by a one week rest period (see Tables 4-6 below). The first dose of each cycle consists of 12 to 24 billion PFU/m$^2$ (administered over 3 hours for course 1 and over 1 hour for all other courses) followed by additional doses of between 24 to 48 billion PFU/m$^2$ (each dose administered over 1 hour). Irinotecan (180 mg/m$^2$ over 90 minutes intravenously) is given every other week beginning during week 2 of cycle 1. Leucovorin (400 mg/m$^2$ over 120 minutes intravenously) is given concurrently with each dose of irinotecan and followed immediately afterwards by an intravenous bolus dose of 5-FU (400 mg/m$^2$) and then a continuous intravenous infusion of 5-FU (2400 mg/m$^2$) over 46 hours using an intravenous pump. Additional 6 week courses (also termed cycles) of NDV, irinotecan, 5-FU and leucovorin are given to the patients.

TABLE 4

Combination of treatment of colorectal cancer patients with NDV, irinotecan (80 to 125 mg/m$^2$), leucovorin, and 5-FU. Cycles of treatment are repeated every 6 weeks.

| Cycle | Week | NDV? | Irinotecan/Leucovorin/5FU? |
|---|---|---|---|
| 1 | 1 | Yes, two doses given 3 days apart | No |
|   | 2 | Yes, 3 doses given 2 days apart | No |
|   | 3 | Yes, two doses given 4 days apart | Yes |
|   | 4 | Yes, one dose | No |
|   | 5 | Yes, two doses given 4 days apart | Yes |
|   | 6 | No | No |
| 2 and higher | 1 | Yes, two doses given 4 days apart | Yes |
|   | 2 | Yes, two doses given 4 days apart | No |
|   | 3 | Yes, two doses given 4 days apart | Yes |
|   | 4 | Yes, two doses given 4 days apart | No |
|   | 5 | Yes, two doses given 4 days apart | Yes |
|   | 6 | No | No |

TABLE 5

Typical Dosing Schedule - Cycle 1

| Monday | Tuesday | Wednesday | Thursday | Friday | Saturday | Sunday |
|---|---|---|---|---|---|---|
| 1 NDV Dose 1 | 2 | 3 | 4 NDV Dose 2 | 5 | 6 | 7 |
| 8 NDV Dose 3 | 9 | 10 NDV Dose 4 | 11 | 12 NDV Dose 5 | 13 | 14 |
| 15 NDV Dose 6 | 16 | 17 Irinotecan/LV/5FU | 18 | 19 NDV Dose 7 | 20 | 21 |
| 22 NDV Dose 8 | 23 | 24 | 25 | 26 | 27 | 28 |
| 29 NDV Dose 9 | 30 | 31 Irinotecan/LV/5FU | 32 | 33 NDV Dose 10 | 34 | 35 |
| 36 | 37 | 38 | 39 | 40 | 41 | 42 |

TABLE 6

Typical Dosing Schedule - Cycles 2 and higher:

| Monday | Tuesday | Wednesday | Thursday | Friday | Saturday | Sunday |
|---|---|---|---|---|---|---|
| 1 NDV Dose 1 | 2 | 3 Irinotecan/LV/5FU | 4 | 5 NDV Dose 2 | 6 | 7 |
| 8 NDV Dose 3 | 9 | 10 | 11 | 12 NDV Dose 4 | 13 | 14 |
| 15 NDV Dose 5 | 16 | 17 Irinotecan/LV/5FU | 18 | 19 NDV Dose 6 | 20 | 21 |
| 22 NDV Dose 7 | 23 | 24 | 25 | 26 NDV Dose 8 | 27 | 28 |
| 29 NDV Dose 9 | 30 | 31 Irinotecan/LV/5FU | 32 | 33 NDV Dose 10 | 34 | 35 |
| 36 | 37 | 38 | 39 | 40 | 41 | 42 |

Example 4

Figure 1:
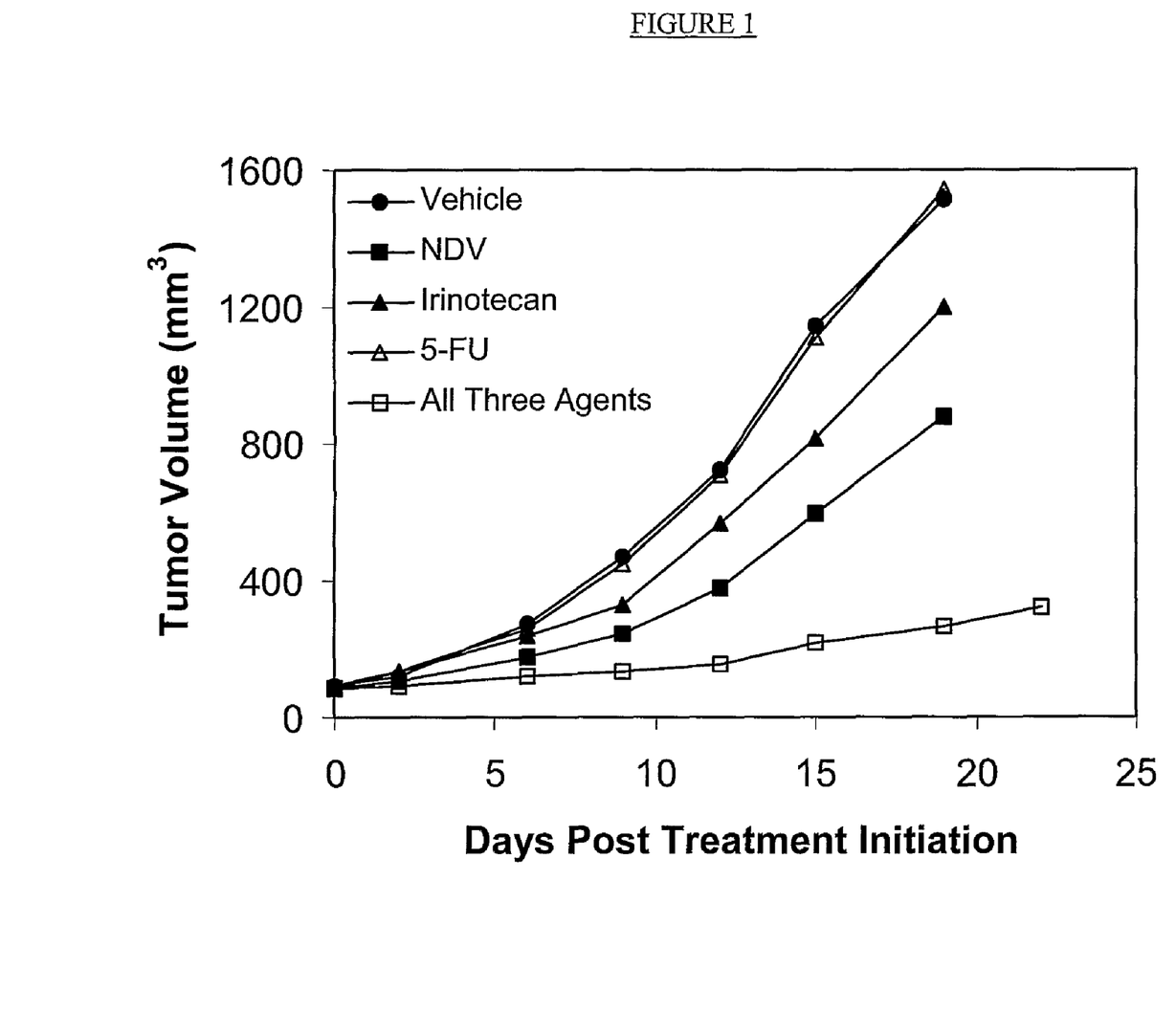
FIG. 1. Graph of average tumor volumes of SW620 colon carcinoma xenografts as a function of time after treatment initiation comparing the activity of the triple combination of NDV (1E+09 PFU)+Irinotecan (25 mg/kg)+5-FU (25 mg/kg) versus either agent alone or to vehicle alone.
Figure 2:
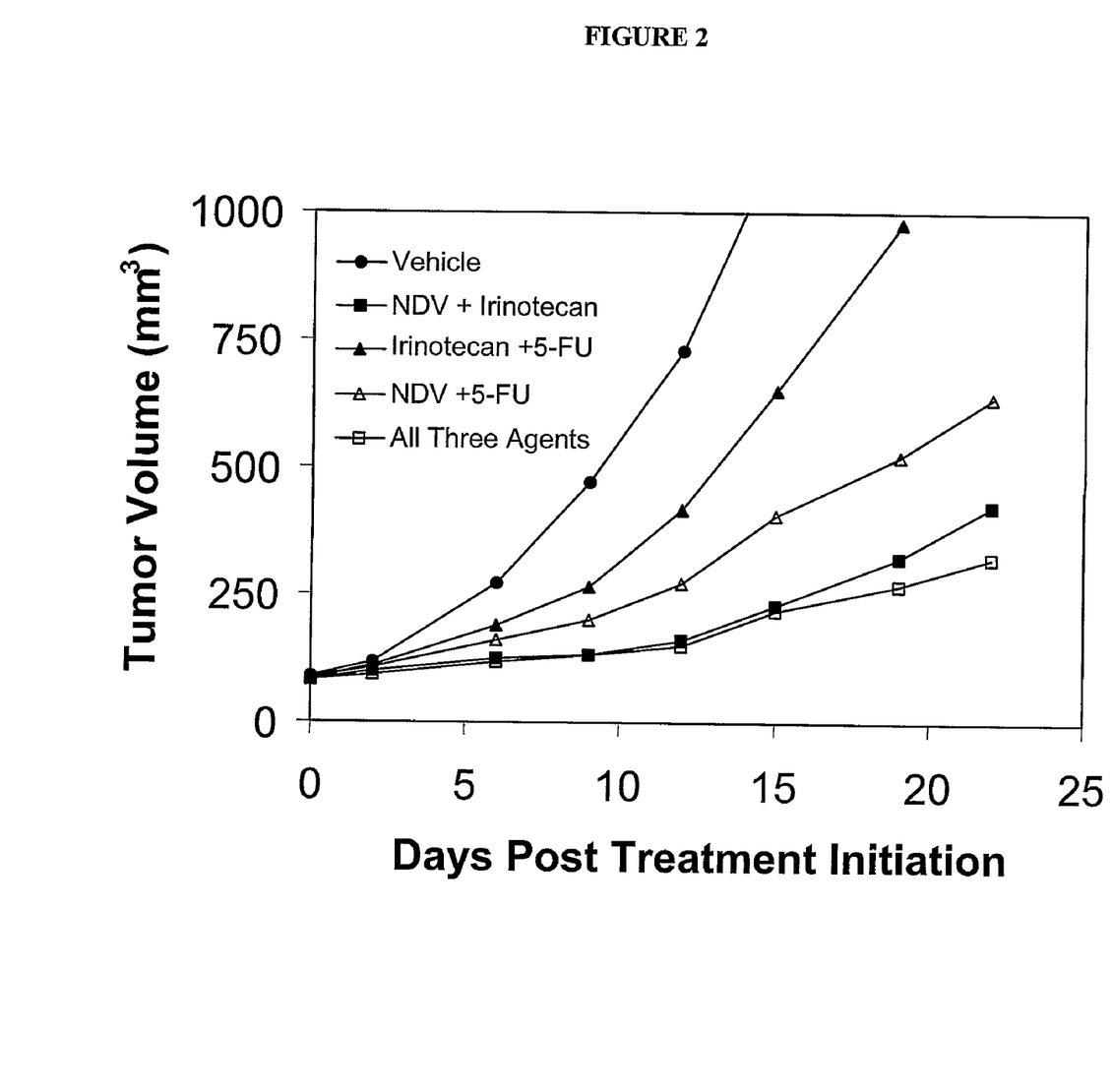
FIG. 2. Graph of average tumor volumes of SW620 colon carcinoma xenografts as a function of time after treatment initiation comparing the activity of the triple combination of NDV (1E+09 PFU)+Irinotecan (25 mg/kg)+5-FU (25 mg/kg) versus each doublet (NDV+Irinotecan; Irinotecan+5-FU; NDV+5-FU) or to vehicle alone.

Athymic mice were injected subcutaneously with 10 million human SW620 colon carcinoma cells (obtained from American Type Culture Collection, Manassas, Va.). Five days later (termed day 0 below) when the subcutaneous tumors were approximately 85 mm³ in size, groups of 11 to 12 animals were randomized into 8 treatment groups:
NDV+Irinotecan
NDV+5-FU
NDV+Irinotecan+5-FU
Irinotecan
5-FU
Irinotecan+5-FU
Vehicle only During Day 0 all mice received either NDV (1E+09 PFU) or vehicle by the intravenous route according to the treatment key provide above. Two days later on Day 2, all mice received a first intraperitoneal injection of either irinotecan (25 mg/kg) or vehicle and then 1 hour later received a second intraperitoneal injection of either 5-FU (25 mg/kg) or vehicle according to the treatment key provided above. The vehicle for NDV was an aqueous solution of 5% mannitol/1% lysine. The vehicle for irinotecan was saline. The vehicle for 5-FU was water for injection. Tumor sizes were periodically determined for all mice using calipers.

As shown in FIG. 1, the combination of NDV+irinotecan+5-FU was markedly superior in terms of antitumor activity to either agent alone or to control vehicle. As shown in FIG. 2, the combination of NDV+irinotecan+5-FU was superior in terms of antitumor activity to either of the treatment doublets (NDV+Irinotecan; Irinotecan+5-FU; NDV+5-FU).

Example 5

Figure 3:
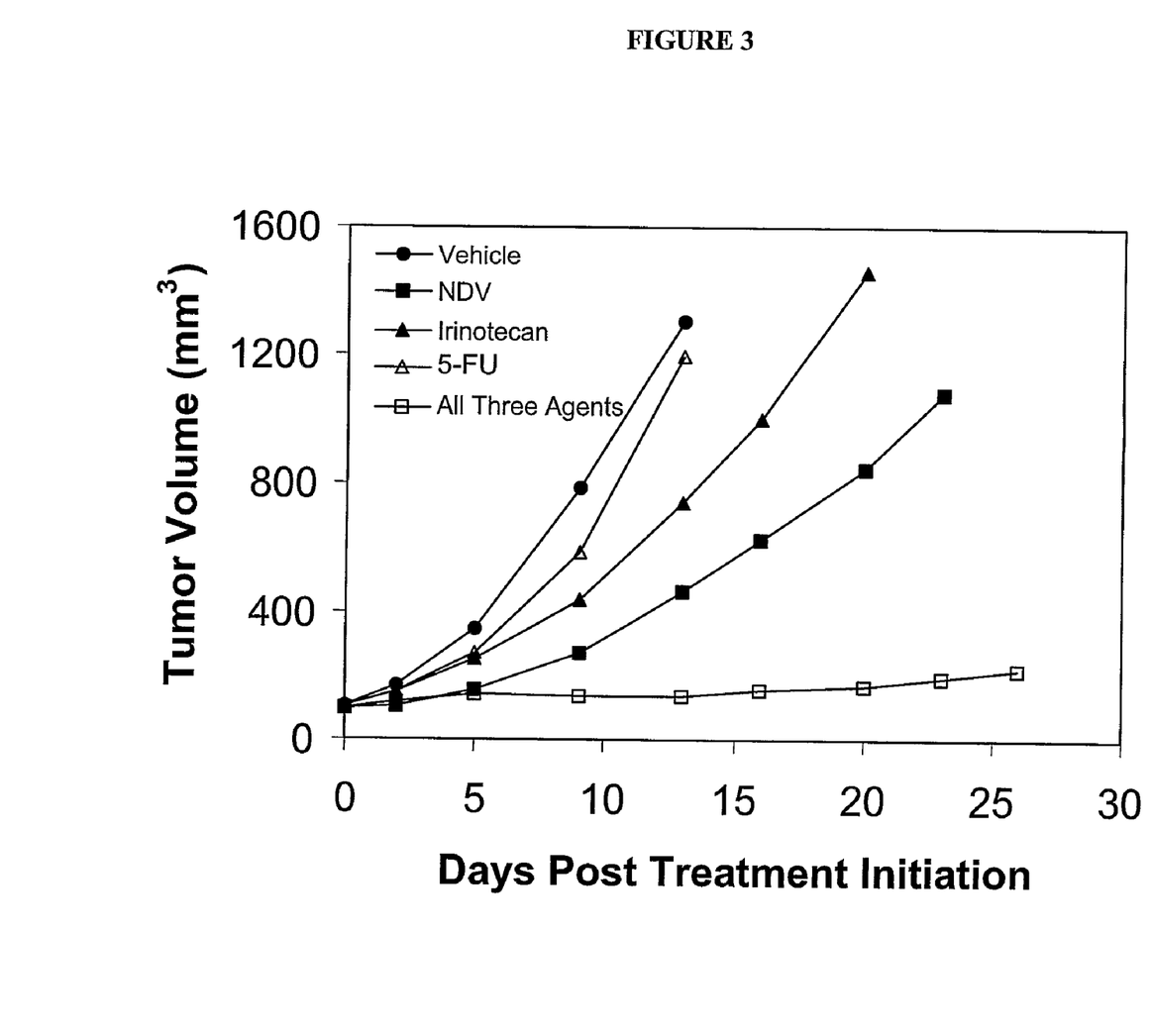
FIG. 3. Graph of average tumor volumes of SW620 colon carcinoma xenografts as a function of time after treatment initiation comparing the activity of the triple combination of NDV (1E+09 PFU)+Irinotecan (15 mg/kg)+5-FU (100 mg/kg) versus either agent alone or to vehicle alone.
Figure 4:
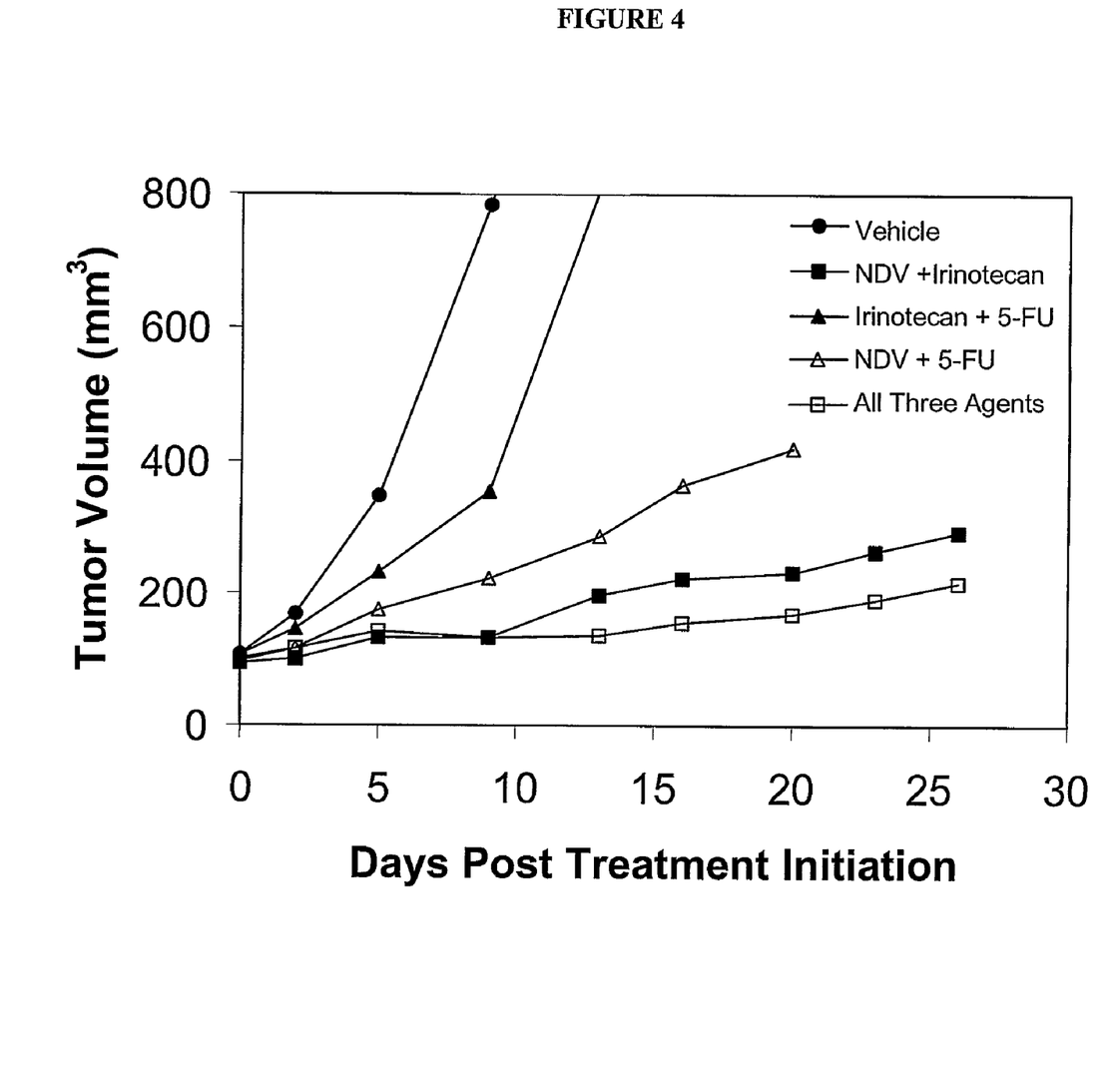
FIG. 4. Graph of average tumor volumes of SW620 colon carcinoma xenografts as a function of time after treatment initiation comparing the activity of the triple combination of NDV (1E+09 PFU)+Irinotecan (15 mg/kg)+5-FU (100 mg/kg) versus each doublet (NDV+Irinotecan; Irinotecan+5-FU; NDV+5-FU) or to vehicle alone.

This experiment was performed as in Example 4, except for the following: (1) treatment was started seven days after subcutaneous inoculation of the SW620 tumor cells; (2) the subcutaneous tumors were approximately 100 mm³ in size, (3) there were 13 mice per treatment group; (4) the dose of irinotecan as 15 mg/kg instead of 25 mg/kg; and (5) the dose of 5-FU was 100 mg/kg instead of 25 mg/kg. As before, animals were randomized into 8 treatment groups:
NDV
NDV+Irinotecan
NDV+5-FU
NDV+Irinotecan+5-FU
Irinotecan
5-FU
Irinotecan+5-FU
Vehicle only As before, during Day 0 all mice received either NDV (1E+09 PFU) or vehicle by the intravenous route according to the treatment key provide above. Two days later on Day 2, all mice received a first intraperitoneal injection of either irinotecan (15 mg/kg) or vehicle and then 1 hour later received a second intraperitoneal injection of either 5-FU (100 mg/kg) or vehicle according to the treatment key provided above. Tumor sizes were periodically determined for all mice using calipers.

As shown in FIG. 3, the combination of NDV+irinotecan+5-FU was again markedly superior in terms of antitumor activity to either agent alone or to control vehicle. As shown in FIG. 4, the combination of NDV+irinotecan+5-FU was again superior in terms of antitumor activity to either of the treatment doublets (NDV+Irinotecan; Irinotecan+5-FU; NDV+5-FU). Furthermore, there was evidence for a synergistic antitumor effect from using all three agents in causing durable tumor regressions. As shown in Table 7, there were more complete tumor regressions (CRs) that were durable (i.e., extending through Day 90) using the triple combination NDV+irinotecan+5-FU than in any other treatment group including any of the treatment doublets (NDV+Irinotecan; Irinotecan+5-FU; NDV+5-FU) and each of the single agents alone.

TABLE 7

Treatment of tumor-bearing mice with the triple combination of NDV + Irinotecan + 5-FU yielded greater durable complete tumor responses than any agent alone or any treatment doublet.

| Treatment | Number of Mice | Durable CRs*, % |
|---|---|---|
| NDV | 13 | 0% |
| NDV + Irinotecan | 13 | 23% |
| NDV + 5-FU | 13 | 0% |
| NDV + Irinotecan + 5-FU | 13 | 46% |
| Irinotecan | 13 | 0% |
| 5-FU | 13 | 0% |
| Irinotecan + 5-FU | 13 | 0% |
| Vehicle Only | 13 | 0% |

*CRs that extended through Day 90.

What is claimed is:

1. A method of treating a mammalian subject having a neoplasm, comprising administering to the subject a replication competent Newcastle Disease virus, a fluoropyrimidine compound, and a camptothecin compound in one or more cycles in a combined amount effective to treat the subject.

2. The method of claim 1, wherein the virus is a mesogenic strain of Newcastle Disease virus.

3. The method of claim 1, wherein the virus is administered intravenously.

4. The method of claim 1 wherein the fluoropyrimidine compound is 5-fluorouracil.

5. The method as in claim 4 further comprising administering to the subject leucovonn.

6. The method as in claim 4 wherein the 5-fluorouracil is administered by continuous infusion over a period of at least 22 hours per dose.

7. The method of claim 1 wherein the camptothecin compound is selected from the group consisting of topotecan, 9-aminocamptothecin, exatecan, karenitecin, rubitecan, lurtotecan, and a homocamptothecin.

8. The method of claim 1, wherein the camptothecin compound is irinotecan.

9. The method of claim 1, wherein the virus is a mesogenic strain of Newcastle Disease Virus, the fluoropyrimidine compound is 5-fluorouracil, and the camptothecin compound is irinotecan.

10. The method of claim 1, wherein the virus, the fluoropyrimidine compound, and the camptothecin compound are administered in two or more cycles.

11. The method of claim 1, wherein the camptothecin compound is administered to the subject from twenty-four hours to one month before administration of the virus.

12. The method of claim 11, wherein camptothecin compound is administered to the subject from twenty-four hours to one week before administration of the virus.

13. The method of claim 1, wherein the camptothecin compound is administered to the subject from twenty-four hours to one month after administration of the virus.

14. The method of claim 13, wherein the camptothecin compound is administered to the subject from twenty-four hours to one week after administration of the virus.

* * * * *